United States Patent [19]
Lindgren et al.

[11] Patent Number: 5,776,347
[45] Date of Patent: Jul. 7, 1998

[54] METHOD FOR REDUCING THE CONTENT OF ORGANIC SOLVENT IN CELLULOSE-REACTIVE HYDROPHOBING AGENTS

[75] Inventors: Erik Lindgren, Bohus; Jeppe Magnusson, Lerum, both of Sweden

[73] Assignee: Eka Nobel AB, Sweden

[21] Appl. No.: 481,530

[22] PCT Filed: Feb. 7, 1994

[86] PCT No.: PCT/SE94/00094

§ 371 Date: Jul. 7, 1995

§ 102(e) Date: Jul. 7, 1995

[87] PCT Pub. No.: WO94/18389

PCT Pub. Date: Aug. 18, 1994

[30] Foreign Application Priority Data

Feb. 15, 1993 [SE] Sweden .................. 9300490
Aug. 19, 1993 [SE] Sweden .................. 9302683

[51] Int. Cl.$^6$ .......................... B01D 15/00
[52] U.S. Cl. ............... 210/691; 210/694; 210/797
[58] Field of Search ................... 210/691, 694, 210/634, 767

[56] References Cited

U.S. PATENT DOCUMENTS 2,369,919 10/1945 Sauer ..................... 260/550
4,522,686 6/1985 Dumas .................... 162/158

FOREIGN PATENT DOCUMENTS 0 074 544    3/1983   European Pat. Off. .
0 550 107 A1 7/1993   European Pat. Off. .
63-264 544   11/1988  Japan .

*Primary Examiner*—Ivars Cintins
*Attorney, Agent, or Firm*—Ralph J. Mancini; Louis A. Morris

[57] ABSTRACT

The present invention generally relates to a method for reducing the content of organic solvent in an aqueous dispersion of a cellulose-reactive hydrophobing agent, prepared by emulsifying a molten cellulose-reactive hydrophobing agent containing organic solvent in an aqueous solution containing one or more emulsifying agents. The method comprises contacting the aqueous dispersion under agitation with a sorbent, said sorbent having the capacity of absorbing or adsorbing organic molecules, or a gas, whereby the solvent is transferred to the sorbent or the gas.

11 Claims, No Drawings

METHOD FOR REDUCING THE CONTENT OF ORGANIC SOLVENT IN CELLULOSE-REACTIVE HYDROPHOBING AGENTS

The present invention relates to a method for reducing the content of organic solvent in cellulose-reactive hydrophobing agents and use of the products obtained. More specifically, the present invention relates to dispersing a hydrophobing agent in water and thereafter contacting it with a sorbent or a gas. By the method of the invention the solvent is transferred from the hydrophobing agent to the aqueous phase and then from the aqueous phase to the sorbent or the gas. The aqueous dispersions containing cellulose-reactive hydrophobing agents prepared according to the invention are used for hydrophobation of paper.

Many kinds of paper are contacted with liquids, primarily aqueous solutions or water vapour. Since the fibres are water-absorbent (hydrophilic), they will absorb water, which reduces the paper strength. This effect can be counteracted by coating the fibres with a water-repellent (hydrophobic) substance, which reduces the possibility of liquid penetrating into the finally-dried web or sheet. Examples of hydrophobated papers are liquid carton board, fine paper and kraft liner.

Hydrophobation is generally performed by adding the hydrophobing agent to the suspension of fibres and water (the stock), so-called stock hydrophobation. To permit rapid and uniform admixture to the stock, the hydrophobing agent is normally dispersed in water.

Especially effective hydrophobing agents are cellulose-reactive hydrophobing agents, since these agents are bonded covalently and hence more strongly to the cellulose fibres than other hydrophobing agents. Thus, alkyl ketene dimers (AKD) are often used to make liquid carton board lactic acid resistant.

In the preparation of an alkyl ketene dimer, organic solvents are used, among other things, for accelerating dimerisation. A portion of the solvents may remain in the alkyl ketene dimer, which may then cause problems before, during or after the use of the alkyl ketene dimer in aqueous dispersions in the paper mills. When storing dispersions, the organic solvents may volatilize and impair the working environment. During the making of hydrophobated paper, the major portion of the residual organic solvents will be transferred to the white water system. The proportion of organic solvent accompanying the stock out on to the wire of the papermaking machine will evaporate, primarily in the drying section, or accompany the finished paper. In the latter case, problems may arise when using the hydrophobic paper as packaging material for solid or liquid foods, tobacco goods and medicines.

It is known to use thermal methods as an attempt to remove the organic solvent in connection with the synthesis. Heating increases the volatility of the solvent as well as the solubility in the melted hydrophobing agent. Cooling reduces the volatility of the solvent as well as the solubility in the melted hydrophobing agent. These opposite effects have made it most difficult to reduce the content of solvent effectively.

According to the present invention there is provided a method for reducing the content of organic solvent in cellulose-reactive hydrophobing agents. Hereby there is achieved a reduction in the proportion of solvent that can be transferred to paper or board, when hydrophobating such materials. Hereby the formation of bonds between the cellulose chains and the cellulose-reactive hydrophobing agent is also enhanced.

The invention thus relates to a method for reducing the content of organic solvent in cellulose-reactive hydrophobing agents, as defined in the claims. According to the inventive method a cellulose-reactive hydrophobing agent and an aqueous dispersion thereof can be prepared where the total content of organic solvent in the hydrophobing agent and the dispersion, respectively, is less than about 0.1% by weight. More specifically, the hydrophobing agent is an alkyl ketene dimer and the solvent is toluene.

The aqueous dispersions containing cellulose-reactive hydrophobing agents prepared according to the inventive method are used for hydrophobation of paper. By the present method the amount of organic solvent in cellulose-reactive hydrophobing agents can be reduced even before the hydrophobing agent reaches the paper mill. Thus, all the above-mentioned problems can be alleviated or completely obviated.

In the preparation of cellulose-reactive hydrophobing agents, the organic solvent used generally is toluene, but also dichloropropane and cyclohexane are conceivable. Suitably, the present invention is employed for reducing the content of toluene. Toluene, like most other organic solvents, is sparingly soluble in water. According to the invention, it has surprisingly been found possible to transfer substantial amounts of organic solvents from the hydrophobic cellulose-reactive hydrophobing agent to the hydrophilic aqueous phase. This can be achieved by first melting the hydrophobing agent and then emulsifying it in an aqueous solution. In this manner, liquid droplets are produced having a size sufficiently small to provide a large contact surface between the liquid phases. When the emulsion is thereafter cooled, the liquid droplets containing the hydrophobing agent solidify and a dispersion is obtained. In the very small particles containing hydrophobing agent, the solubility of the organic solvents is lower than in corresponding liquid droplets, whereby the solvents are transferred to the ambient aqueous phase. By thereafter contacting the aqueous dispersion with a sorbent or a gas, the solvent content in the aqueous phase can be reduced to the desired low level.

The content of organic solvent in cellulose-reactive hydrophobing agents may in some cases be as high as 3% by weight. Usually, the total content of organic solvent is from 0.2 to 2% by weight. By the present invention, it is possible to prepare cellulose-reactive hydrophobing agents and aqueous dispersions containing such hydrophobing agents where the total content of organic solvents is below about 0.1% by weight. Suitably, the total content is from 0.01 to 0.08% by weight and preferably from 0.02 to 0.06% by weight. By the present method, the total content of solvent in the dispersion largely remains the same if the sorbent is left in the finished dispersion. When using the dispersion at normal temperatures, the organic molecules of the solvent will however be solidly bonded to the sorbent, especially if this is a zeolite. Therefore, the total content of free organic solvent in the dispersion may be below about 0.1% by weight at 20° C., even when the sorbent is included in the finished dispersion. Suitably, the total content of free organic solvent in the dispersion is below 0.06% by weight at 20° C.

The term "cellulose-reactive hydrophobing agent" as used herein relates to synthetically prepared hydrophobing agents which are covalently bonded to the cellulose fibres in the stock. Examples of such cellulose-reactive hydrophobing agents are alkyl ketene dimers (AKD), cyclic dicarboxylic anhydrides, such as alkenyl succinic anhydride (ASA), carbamoyl chloride and stearic anhydride. Suitably, use is made of alkyl ketene dimers or cyclic dicarboxylic anhydrides, preferably alkyl ketene dimers.

Alkyl ketene dimers (AKD) is a mixture of different compounds of the general formula

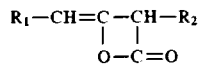

wherein $R_1$ and $R_2$ are hydrophobic hydrocarbon groups having from about 6 to about 30 carbon atoms and generally consisting of alkyl groups having from 12 to 20 carbon atoms, such as hexadecyl and octadecyl groups.

Cyclic dicarboxylic anhydrides can be characterised by the general formula

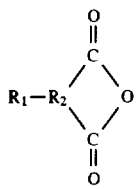

wherein $R_2$ is a dimethylene or trimethylene radical and $R_1$ is a hydrocarbon group which have more than 7 carbon atoms and may consist of an alkyl, alkenyl, aralkyl or aralkenyl group. The cyclic dicarboxylic anhydrides predominantly used commercially are alkyl and alkenyl succinic anhydrides (ASA), especially isooctadekenyl succinic anhydride.

Even if the advantages of the present method can be achieved by any cellulose-reactive hydrophobing agent, the present invention will be described hereinafter with reference to alkyl ketene dimer (AKD).

The preparation of alkyl ketene dimers is commenced by reacting a fatty acid or, more generally, a mixture of fatty acids with a chlorinating agent to a fatty acid chloride. The fatty acid primarily used is stearic acid ($C_{17}H_{35}COOH$). The chlorinating agent may be e.g. thionyl chloride, phosphorous trichloride, phosphorous pentachloride or phosgene. One example of the initial reaction is shown in Formula 1 where stearic acid is reacted with phosgene:

The fatty acid chloride obtained is thereafter mixed with an alkylamine acting as chlorine acceptor. The alkylamine used may be e.g. triethylamine or dimethylcyclohexylamine. One example of this reaction step is shown in Formula 2 where the fatty acid chloride obtained above is dimerised by the presence of triethylamine:

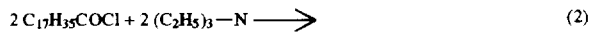

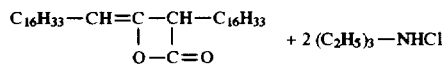

In the second step, an organic solvent, generally toluene, is used for accelerating the dimerisation. After completion of the reaction in the second step, the amine hydrochloride is allowed to settle before being drawn off. The organic solvent is removed substantially by distillation of the remaining reaction solution containing alkyl ketene dimers. Certain residual amounts of the solvent will however remain, which causes problems when using the finished alkyl ketene dimer existing in the form of a wax.

The preparation of alkyl ketene dimers may be performed continuously or batchwise.

Normally, the alkyl ketene dimers are used in the paper mill in the form of an aqueous dispersion. The content of cellulose-reactive hydrophobing agent in the finished dispersion may range from about 5 to about 30% by weight. Suitably the content is from 6 to 20% by weight and preferably from 9 to 16% by weight.

According to the present method the content of organic solvent in cellulose-reactive hydrophobing agents is reduced by dispersing the hydrophobing agent in water whereby the solvent is transferred to the aqueous phase, whereupon the aqueous dispersion is contacted with a sorbent or a gas whereby the solvent is transferred to the sorbent or the gas. By a suitable combination of contact time, temperature and amount of sorbent or gas, the content of solvent in the aqueous phase can thus be reduced to a desirable low level. More specifically, the aqueous dispersion is prepared by heating a wax containing alkyl ketene dimers to above the melting point, which is about 50° C. The molten wax containing alkyl ketene dimers is thereafter admixed to an aqueous solution containing one or more emulsifying agents, thereby to obtain an emulsion. The aqueous solution is maintained in continuous motion, so that liquid droplets of wax having a size of from about 0.3 to about 3 µm are formed.

The molten wax can be admixed and maintained in motion by means of any equipment that is suited for preparing aqueous emulsions. However, it has been found especially suitable to use a high-turbulence mixer or a homogeniser, thereby to obtain high shear forces.

During emulsification, the temperature may range from about 55° to about 95° C., suitably from 65° to 80° C. During emulsification, the pressure may range from about 50 to about 500 bars.

The emulsifying agents that can be used in the present invention are conventional anionic, cationic or amphoteric emulsifying agents or mixtures thereof. According to preferred embodiments employing AKD as the cellulose-reactive hydrophobing agent, use is usually made of one or more anionic emulsifying agents, such as sodium lignosulphonate or sodium salts of condensed aromatic sulphonic acids, for example condensation products of formaldehyde with sodium naphtalene sulphonate. The amount of emulsifying agent added may range from about 0.1 to about 20% by weight based on dry cellulose-reactive hydrophobing agent, suitably from 0.2 to 10% by weight based on dry cellulose-reactive hydrophobing agent.

Examples of suitable protective colloids are cationic polymers, which can be natural, such as waxy maize starch, or synthetic, such as polyamines or polyacrylamides. The amount of natural polymer added may range from about 5 to about 70% by weight, suitably from 10 to 50% by weight, based on dry cellulose-reactive hydrophobing agent. The amount of synthetic polymer added may range from about 5 to about 100% by weight, suitably from 10 to 75% by weight, based on dry cellulose-reactive hydrophobing agent.

Once the liquid droplets containing alkyl ketene dimers have a suitable size, the temperature in the aqueous solution is lowered to a temperature of from about 5° to about 30° C., suitably 10°-20° C. As a result, the liquid droplets containing molten wax will solidify and a dispersion is obtained. The aqueous dispersion is thereafter contacted with a sorbent or a gas, suitably a sorbent. The sorbent may remain in the finished dispersion, but it is preferred that the sorbent with sorbed solvent is removed from the dispersion.

The dispersion can be maintained in motion by any equipment suited for producing aqueous dispersions. Suitably, use is made of the same equipment as was used for preparing the emulsion. Furthermore, it is important that the dispersion is maintained in motion also after it has been contacted with the sorbent or the gas. In this way, the transfer of solvent from the aqueous phase to the sorbent or the gas is improved as compared with the case of a stationary dispersion.

The time of contact between dispersion and sorbent is a function of the content of solvents, the content of alkyl ketene dimers in the dispersion, the capacity of the sorbent to sorb the solvents in the aqueuous dispersion, and further depends on whether the sorbent is to remain in the dispersion or not. Suitably, this time ranges from about 0.5 to about 60 min, preferably from 1 to 30 min.

The flow velocity of the gas is a function of the content of solvents, the content of alkyl ketene dimers in the dispersion, the capacity of the gas to absorb the solvents, the extent of mixing in the solution and the bubble size.

The gas used for removing the solvents from the aqueous dispersion may be air or inert gases, such as nitrogen, helium or argon. Suitably, the gas is air or nitrogen gas. Further, the moisture content of the gas suitably is low, since this increases its capacity to absorb organic molecules. Thus, the moisture content of the gas suitably is less than about 25 g $H_2O/m^3$ gas at 1 bar and 25° C. Moreover, the temperature of the gas suitably ranges from about 15° to about 40° C., since the alkyl ketene dimers will then exist as a dispersion. This makes it easier to remove toluene than if the alkyl ketene dimers exist as an emulsion, since the solubility of the solvent is lower in solid particles than in corresponding liquid droplets.

The sorbent may be any solid material having the capacity of sorbing organic molecules on the surface (adsorbent) or within the material (absorbent). Examples of suitable sorbents are zeolites, active carbon and silica gel. Preferably, use is made of a zeolite, since such compounds have a high capacity of sorbing the organic molecules at issue. In addition, due to its inert nature and other properties, a zeolite will affect only to a very small extent e.g. the colour and the consistency of the hydrophobing agent and the aqueous dispersion. The zeolite may remain in the finished dispersion, since the solvents are very strongly sorbed to the zeolite particles. If the zeolite remaining in the finished dispersion is not saturated with toluene, there is a capacity of sorbing additional toluene or other organic molecules. Thus, the zeolite can reduce the transfer of substances causing taste or substances that are injurious to health, from the finished hydrophobated paper to the environment. This can be used e.g. in liquid carton board. The zeolite is also suitable in those cases where the sorbent is to be removed from the dispersion, since the separation can take place in a simple manner after completion of the sorption. Separation takes place by interrupting the agitation of the aqueous dispersion so as to allow the zeolite to settle.

Zeolites are inorganic crystalline compounds, substantially consisting of $SiO_2$ and $Al_2O_3$ in tetrahedral coordination. However, the term "zeolite" as used in this context also relates to other crystalline compounds of zeolite structure, such as aluminium phosphates. One essential property of the zeolites of the present invention is their limited water-adsorbing capacity. Such a hydrophobic (water-repellent) character at the same time means an increased capacity of adsorbing organic compounds. Zeolites having a capacity of adsorbing, for example, aromatic compounds and, hence, the most essential solvents that are used in the preparation of alkyl ketene dimers, primarily are zeolites having a high molar ratio of $SiO_2$ to $Al_2O_3$ in tetrahedral coordination. In the present invention, it is of importance that the molar ratio of $SiO_2$ to $Al_2O_3$ in tetrahedral coordination is at least about 10:1. Suitably, the molar ratio is from 15:1 to 100:1.

In most zeolites, the water-repellent capacity may be modified to a certain extent by different treatments of their surface, such as heating in ammonia atmosphere, in water vapour or air. One method of determining the hydrophobicity of the zeolite after such treatments is the so-called Residual Butanol Test, which is described in British Patent Specification 2,014,970. In the present invention, the hydrophobicity of the zeolite, characterised by the residual butanol content, should be less than about 0.6% by weight. Suitably, the residual butanol content ranges from 0.003 to 0.5% by weight, preferably from 0.02 to 0.4% by weight.

Zeolites which, optionally after a certain modification, exhibit a high degree of hydrophobicity and therefore are capable of effectively sorbing the organic solvents used for preparing cellulose-reactive hydrophobic agents are those of pentasil type, faujasite type, mordenite, erionite and zeolite L. Suitably, the hydrophobic zeolites are of pentasil type. The zeolite of pentasil type suitably is ZSM-5 or ZSM-11 and preferably ZSM-5.

For a good sorbing effect, the zeolite must exhibit a large total sorbing surface in the dispersion. This is achieved, inter alia, if the particles are small. Suitably, the particle size of the zeolite therefore is less than about 10 μm and preferably ranges from 1 to 6 μm.

The amount of sorbent added is primarily a function of the amount of solvents in the aqueous dispersion, the total sorbing surface of the sorbent as well as the desired content of solvents in the finished hydrophobing agent or the dispersion containing such an agent. If the solvent-containing sorbent is to remain in the aqueous dispersion, the amount of sorbent added is also affected by the need of a remaining sorbing capacity in the finished paper or board. The added amount of sorbent may range from about 3 to about 1000 g/kg of dry cellulose-reactive hydrophobing agent. Suitably, the amount of sorbent added ranges from 5 to 500 g/kg of dry cellulose-reactive hydrophobing agent, preferably from about 10 to 300 g/kg of dry cellulose-reactive hydrophobing agent.

The invention and its advantages will be further elucidated in the following Examples, which are only intended to illustrate the invention without restricting it in any way. The values indicated in parts and per cent in the description, the claims and the Examples are parts by weight and per cent by weight, respectively, unless otherwise stated.

EXAMPLE 1

An aqueous dispersion containing alkyl ketene dimers (AKD) having a low toluene content was prepared according to the invention. 450 g of AKD wax, manufactured by Eka Nobel AB, was melted at 70° C. and mixed with 2470 g of water and 74 g of sodium lignosulphonate and starch as emulsifying agent and protective colloid, respectively. The aqueous solution was passed through an emulsifier of the valve homogeniser type at a pressure of 250 bars so as to obtain an emulsion. The temperature was immediately lowered to 20° C. and the pressure to atmospheric pressure. The finished dispersion containing 0.5% by weight of toluene was contacted with a hydrophobic zeolite and active carbon, respectively, under agitation. In both cases, the contact time was about 20 min and the amount of sorbent 10% by weight based on the dry alkyl ketene dimer. The aqueous dispersion of alkyl ketene dimers had an alkyl ketene dimer content of 15% by weight and a dry solids content of 17.5% by weight.

The hydrophobic zeolite was of ZSM-5 type. The molar ratio of $SiO_2$ to Al2O3 in tetrahedral coordination was 32 and the residual butanol content 0.14% by weight.

The active carbon was of standard type, characterised by a particle size of between 3 and 5 mm.

The mixture of alkyl ketene dimer and sorbent was left for 30 min before centrifugation. The sorbent was separated as a lower phase while the upper phase was analysed for toluene according to the so-called hot method. This method means that a given amount of solution is poured into a test tube which is sealed. After shaking the test tube for 1 min followed by thermostating at 95° C. for 40 min. a gas quantity was withdrawn from above the sample and immediately analysed in a gas chromatograph with respect to toluene. The toluene content is indicated as counts/g of alkyl ketene dimer. As a reference, use was made of the dispersion containing alkyl ketene dimer before contact with any of the sorbents.

TABLE I

| Sample No. | Sorbent | Toluene content counts · 10-6/g | Reduction % |
| --- | --- | --- | --- |
| 1 | — | 14.9 | — |
| 2 | Active carbon | 0.41 | 97.2 |
| 3 | Zeolite | 0.48 | 96.7 |

As evident from Table 1. the toluene content in an aqueous dispersion containing cellulose-reactive hydrophobing agent can be lowered by about 97% by being contacted with a solid sorbent.

EXAMPLE 2

The aqueous dispersion used in Example 1 was contacted with flowing air, thus reducing the toluene content. The alkyl ketene dimer dispersion was poured into a glass flask with a bubble tube. The temperature of the dispersion was 20° C. Air having a temperature of 20° C. was bubbled through the dispersion at a flow rate of 410 ml/min. The air leaving the glass flask was analysed for toluene according to the hot method described above. The toluene content is indicated as counts/g of alkyl ketene dimer. which is converted into accumulated amount of toluene in total volume of air bubbled through the glass flask. At the beginning of the test. the alkyl ketene dimer contained a total of 161 mg of toluene.

TABLE II

| Sample No. | Air volume litre | Amount of toluene in air, mg | Reduction % |
| --- | --- | --- | --- |
| 1 | 1 | 8.4 | 5 |
| 2 | 3 | 22.1 | 14 |
| 3 | 5 | 34.3 | 21 |
| 4 | 8 | 52.1 | 32 |
| 5 | 10 | 62.5 | 39 |

TABLE II-continued

| Sample No. | Air volume litre | Amount of toluene in air, mg | Reduction % |
| --- | --- | --- | --- |
| 6 | 14 | 80.1 | 50 |
| 7 | 18 | 94.6 | 59 |
| 8 | 30 | 123 | 76 |
| 9 | 50 | 144 | 89 |
| 10 | 70 | 154 | 96 |
| 11 | 90 | 159 | 99 |

As evident from Table 2. the content of toluene in a celullose-reactive hydrophobing agent can be practically eliminated by contacting an aqueous dispersion of the hydrophobing agent with flowing air.

We claim:

1. A method for reducing the content of organic solvent in an aqueous dispersion of a cellulose-reactive hydrophobing agent, prepared by emulsifying a molten cellulose-reactive hydrophobing agent containing organic solvent in an aqueous solution containing one or more emulsifying agents, and then solidifying said hydrophobing agent by means of cooling, wherein said method comprises contacting the aqueous dispersion under agitation with a sorbent, said sorbent having the capacity of absorbing or adsorbing organic molecules, or a gas, whereby the solvent is transferred to the sorbent or the gas.

2. The method of claim 1 wherein the cellulose-reactive hydrophobing agent is an alkyl ketene dimer.

3. The method of claim 1 wherein the organic solvent is toluene.

4. The method of claim 1 wherein the sorbent is a zeolite, active carbon or a silica gel.

5. The method of claim 4 wherein the sorbent is a zeolite.

6. The method of claim 5 wherein the zeolite has a hydrophobicity of below about 0.6% by weight residual butanol as determined by the Residual Butanol Test.

7. The method of claim 1 wherein the sorbent is separated after it has been contacted with the aqueous dispersion.

8. The method of claim 1 wherein the gas is bubbled through the aqueous dispersion.

9. The method of claim 8 wherein the gas is air, nitrogen, helium or argon.

10. The method of claim 1 wherein the gas is air, nitrogen, helium or argon.

11. The method of claim 1 wherein the total content of organic solvent in the aqueous dispersion containing a cellulose-reactive hydrophobing agent is reduced to less than about 0.1% by weight.

* * * * *